(12) United States Patent
Yamamoto et al.

(10) Patent No.: US 6,748,049 B1
(45) Date of Patent: Jun. 8, 2004

(54) X-RAY CAMERA

(75) Inventors: Toshiyoshi Yamamoto, Hyogo (JP); Takuo Shimada, Hyogo (JP); Atsushi Sakata, Osaka (JP); Kazuya Kondo, Osaka (JP); Yoshihiro Ino, Hyogo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/701,479

(22) PCT Filed: Mar. 23, 2000

(86) PCT No.: PCT/JP00/01784
§ 371 (c)(1),
(2), (4) Date: Jan. 22, 2001

(87) PCT Pub. No.: WO00/57786
PCT Pub. Date: Oct. 5, 2000

(30) Foreign Application Priority Data

Mar. 29, 1999 (JP) ............................................. 11-85844

(51) Int. Cl.$^7$ ................................................. H05G 1/61
(52) U.S. Cl. ........................................ 378/98.7; 378/62
(58) Field of Search ............................. 378/98.7, 98.8, 378/18, 207, 205, 8, 62; 382/168, 169, 254, 274

(56) References Cited

U.S. PATENT DOCUMENTS

| | | | | |
|---|---|---|---|---|
| 5,434,902 A | * | 7/1995 | Bruijns | 378/98.7 |
| 6,208,710 B1 | * | 3/2001 | Nagai | 378/108 |
| 6,263,044 B1 | * | 7/2001 | Joosten | 378/98.7 |
| 6,292,535 B1 | * | 9/2001 | Williams et al. | 378/98.8 |

FOREIGN PATENT DOCUMENTS

| | | |
|---|---|---|
| JP | 63-203144 | 8/1988 |
| JP | 04168883 | 6/1992 |
| JP | 5-42130 | 2/1993 |
| JP | 07148143 | 6/1995 |
| JP | 08117212 | 5/1996 |
| JP | 08117213 | 5/1996 |
| JP | 08215190 | 8/1996 |
| JP | 8-215190 | 8/1996 |
| JP | 10-213667 | 8/1998 |

* cited by examiner

Primary Examiner—David V. Bruce
Assistant Examiner—Hoon Song
(74) Attorney, Agent, or Firm—McDermott, Will & Emery

(57) ABSTRACT

X-ray camera of the present invention comprises an X-ray irradiation unit, an X-ray image sensor, a controller having a correction factor setting unit, a correction factor storage unit and a correctional operation unit, and a display unit. The X-ray image sensor in the above configuration comprises a sensor such as CCD, TFT, and the like having a scintillator on a surface thereof, and a substrate having the sensor mounted thereon. The correction factor setting unit obtains a value La/Ln by dividing a predetermined brightness reference value La set beforehand by a brightness value Ln of an arbitrary pixel "n", and sets the obtained value as a correction factor for each pixel. The correction factor storage unit stores the correction factor set by the correction factor setting unit. The correctional operation unit obtains the correction factor from the correction factor storage unit, and performs a corrective operation.

16 Claims, 6 Drawing Sheets

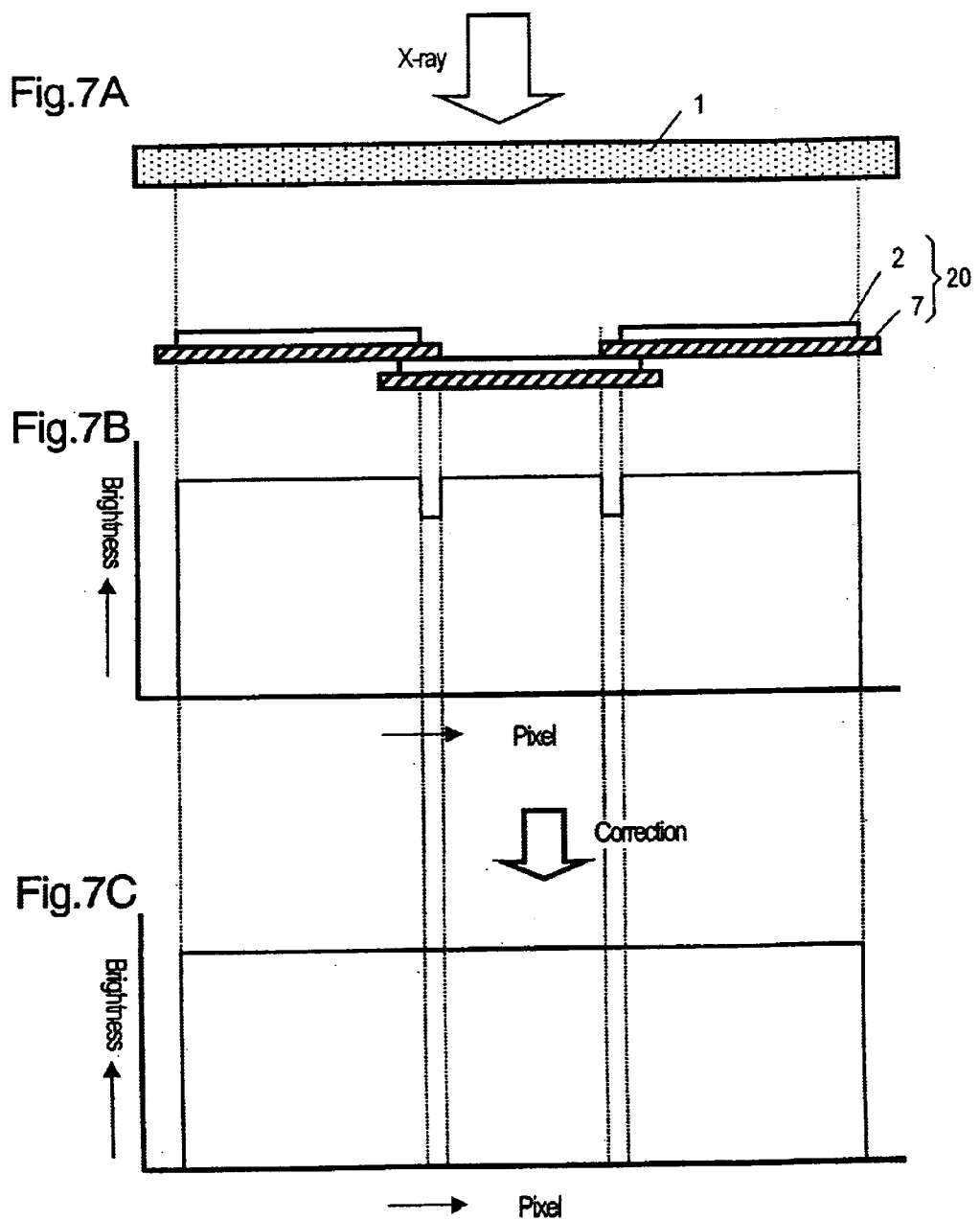

X-RAY CAMERA

FIELD OF THE INVENTION

The present invention relates to X-ray camera used in medical diagnosis, dentistry, and the like.

BACKGROUND OF THE INVENTION

X-ray camera of the kind known heretofore include:
- conventional X-ray camera used in medical diagnosis for taking photographs of joint regions such as hands and feet, chest, and so on; and
- intraoral X-ray camera and panoramic X-ray camera used in dentistry.

As for the method of displaying images, it has been a general practice to print out X-ray images on films for use as monochrome pictures.

In recent years however, there evolved another method of displaying an image that uses a variety of digital techniques after transferring an X-ray image onto a special fluorescent film.

Some of the techniques proposed for use in the method of displaying images include:
- a CR (Computed Radiography) technique, in which a fluorescent image is read by using laser, and stored as a digital image;
- a technique, in which a combination of charge coupled device (hereinafter referred to as "CCD") and fluorescent material is used to read directly as a digital image in a similar manner as the video photography; and
- a technique, in which a combination of TFT (Thin Film Transistor) panel and photo diode, in combination with fluorescent material is used to read directly as a digital image in a similar manner as the video photography.

Unlike the case of using films, an X-ray camera that uses the digital techniques as above represents a method of expression, in that the equipment accurately reads an X-ray photographic image pixel by pixel, and composes a complete image by realigning again the individual pixel data obtained therefrom on a display device.

For this reason, any defect of pixels of the CCD, the TFT, and the like, manufacturing dispersion of the reading circuits for individual pixels, and so on are reflected just as they are in the pixel data. This has been the failure peculiar to the digital X-ray photography that deteriorates picture quality of display images as typified by slight variations in brightness.

SUMMARY OF THE INVENTION

The present invention is to solve the foregoing problem of the prior art technique, and intended to improve picture quality of X-ray photographic images.

To achieve the above-described problem, X-ray camera of this invention comprises:
- an X-ray irradiation unit;
- an X-ray image sensor;
- a controller comprising a correction factor setting unit, a correction factor storage unit, and a correctional operation unit; and
- a display unit.

The X-ray image sensor in the above configuration comprises:
- a sensor such as CCD, TFT, and the like having a scintillator on a surface of it; and
- a substrate having the sensor mounted thereon.

The correction factor setting unit (hereinafter referred to simply as "setting unit") obtains a value La/Ln for an arbitrary pixel "n" by dividing a predetermined brightness reference value La set beforehand by a brightness value Ln of the arbitrary pixel "n", and sets the obtained value as a correction factor of each pixel.

The correction factor storage unit (hereinafter referred to simply as "storage unit") stores the correction factor set by the setting unit.

The correctional operation unit (hereinafter referred to simply as "operation unit") obtains the correction factor from the storage unit, and performs a corrective operation.

The display unit displays an image, which is corrected by the operation unit.

The X-ray camera of this invention, with the configuration as described above, cancels errors in brightness caused by inherent dispersion of the sensors and image detector circuits peculiar to the X-ray camera, by making correction of brightness of the image obtained in the photography, and thereby it can realize substantial improvement in quality of the X-ray image.

BRIEF DESCRIPTION OF THE DRAWINGS

FIG. 7A is an expository illustration depicting operation of X-ray camera having a sensor configuration described in a fourth exemplary embodiment;

FIG. 7B is a diagrammatic illustration showing an example of brightness distribution of an image, obtained with the X-ray image sensor 2 of the fourth exemplary embodiment, along a row of pixels in a one-dimensional direction; and FIG. 7C is a diagrammatic illustration showing the brightness distribution after corrected according to the fourth exemplary embodiment.

THE BEST MODE FOR CARRYING OUT THE INVENTION

With reference to accompanying figures, X-ray camera of the present invention will be described hereinafter.

First Exemplary Embodiment

Referring now to FIG. 1 through FIG. 5, a first exemplary embodiment of this invention is described hereinafter.

Figure 1:
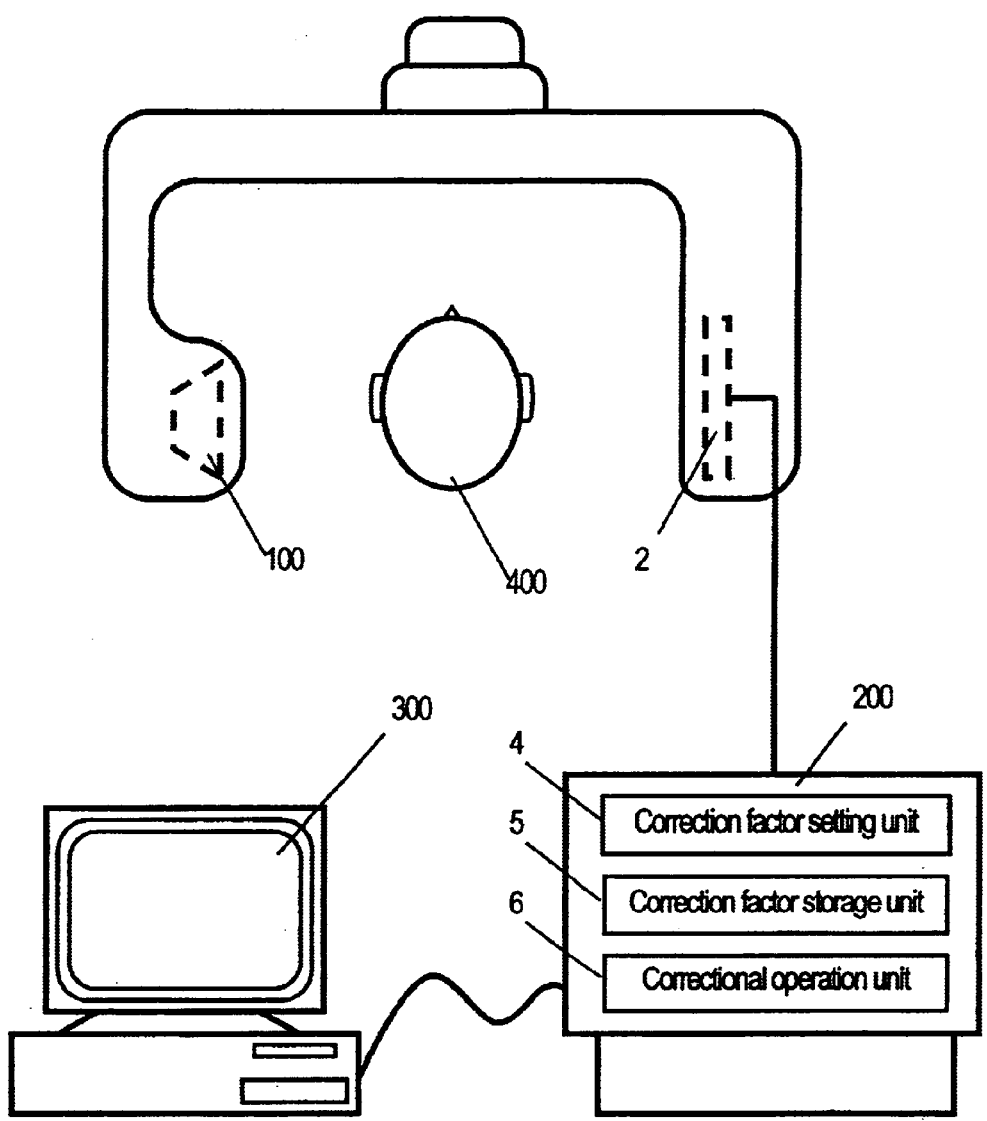
FIG. 1 is an illustration depicting a configuration of X-ray camera of a first exemplary embodiment.

FIG. 1 is an illustration depicting a configuration of the X-ray camera of the first exemplary embodiment of this invention. As shown in FIG. 1, the X-ray camera of the first exemplary embodiment comprises:

an X-ray irradiation unit 100;

an X-ray image sensor 2;

a controller 200 comprising a setting unit 4, a storage unit 5, and an operation unit 6; and a display unit 300.

A reference numeral 400 shown in FIG. 1 schematically illustrates a subject for the X-ray equipment.

Figure 2A:
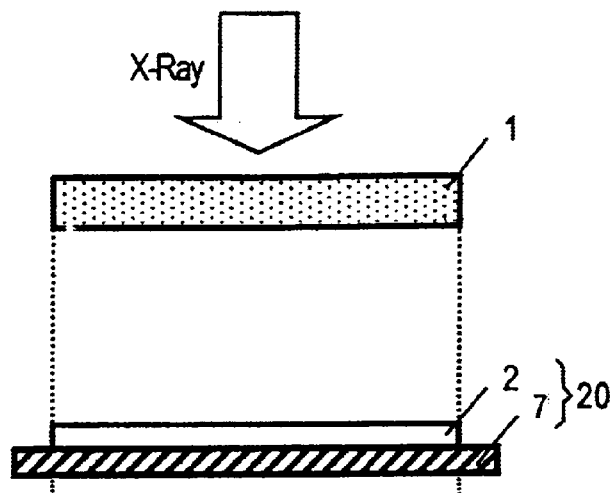
FIG. 2A is a diagrammatic illustration showing an aspect of taking an X-ray image of a subject 1 serving as a reference.

As shown in FIG. 2A, an X-ray image sensor unit (hereinafter referred to simply as "sensor unit") 20 in the above configuration comprises:

an X-ray image sensor (hereinafter referred to simply as "sensor") 2 such as CCD, TFT, and the like having a scintillator on a surface of it (not shown in the figure); and a substrate 7 having the sensor 2 mounted thereon.

A corrective operation of brightness of a photographed image displayed in the display unit 300 is described now.

FIG. 2A diagrammatically illustrates an aspect of taking an X-ray image of a reference subject 1. In FIG. 2A, when X rays are irradiated to the reference subject 1, the X rays penetrated through the subject 1 are converted into light signal by the scintillator (not show in the figure), and detected as an image by the sensor 2 mounted on the substrate 7.

Figure 2B:
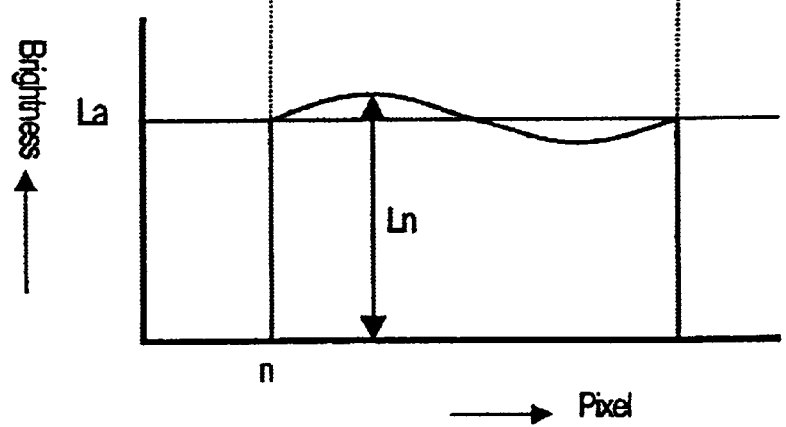
FIG. 2B is a diagrammatic illustration showing an example of brightness distribution of the image of the subject 1 obtained with an X-ray image sensor 2 along a row of pixels in a one-dimensional direction.

FIG. 2B diagrammatically illustrates an example of brightness distribution along a row of pixels in a one-dimensional direction of the image of the reference subject 1 obtained by the sensor 2. Fundamentally, value of brightness shall be invariant from pixel to pixel. However, the value of brightness varies slightly from pixel to pixel as shown in FIG. 2B, due to an inherent dispersion of the sensor 2, detector circuits (not show in the figure), or the like.

Therefore, the setting unit 4 obtains a value La/Ln for an arbitrary pixel "n" by dividing a predetermined brightness reference value La by a brightness value Ln of the arbitrary pixel "n", and sets the obtained value as a correction factor of each pixel. Here, the brightness reference value La is a design value of the sensor 2, and therefore the value of brightness that should naturally be output.

The correction factor for each pixel obtained by taking the X-ray image of the reference subject 1 is stored in the storage unit 5.

Described next pertains to a corrective operation carried out according to the correction factor obtained above for brightness of an image taken by X-ray photographing a step-wise configuration model 3, which typifies a subject body. The step-wise configuration model 3 is composed of aluminum and the like, to represent a subject body in place of a human body.

Figure 3A:
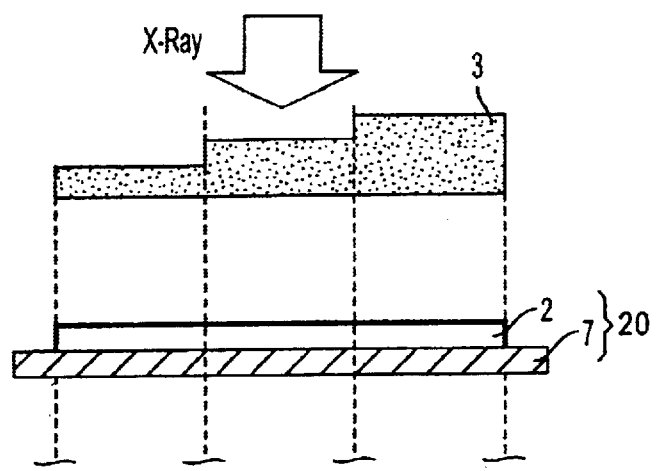
FIG. 3A is a diagrammatic illustration showing an aspect of taking an X-ray image of a model subject.
Figure 3B:
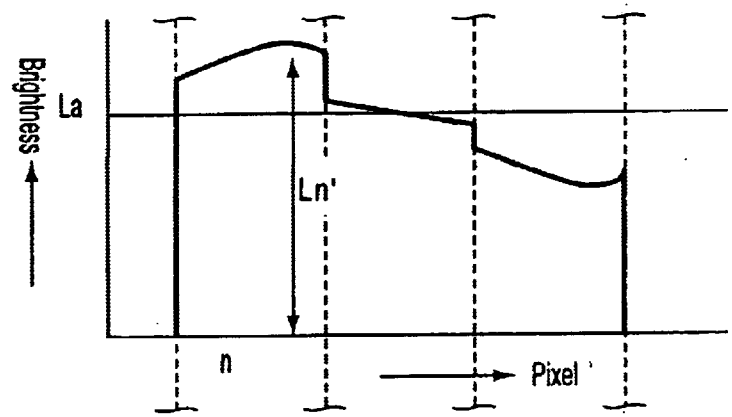
FIG. 3B is a diagrammatic illustration showing an example of brightness distribution of the image, obtained with the X-ray image sensor by taking photograph of the model of step-wise configuration, along a row of pixels in a one-dimensional direction.

FIG. 3A diagrammatically illustrates an aspect of taking an X-ray image of the model serving as a subject body. In FIG. 3A, when X rays are irradiated to the step-wise configuration model 3, the X rays penetrated through the step-wise configuration model 3 are converted into light signal by the scintillator (not show in the figure), and detected as an image by the sensor 2 mounted on the substrate 7. FIG. 3B diagrammatically illustrates an example of brightness distribution along a row of pixels in a one-dimensional direction of the image obtained with the sensor 2 by taking photograph of the step-wise configuration model 3. Fundamentally, value of brightness shall be invariant from pixel to pixel. However, the value of brightness varies slightly from pixel to pixel as shown by a line Ln' in FIG. 3B, due to an inherent dispersion of the X-ray image sensor 2, detector circuits (not show in the figure), or the like.

Figure 3C:
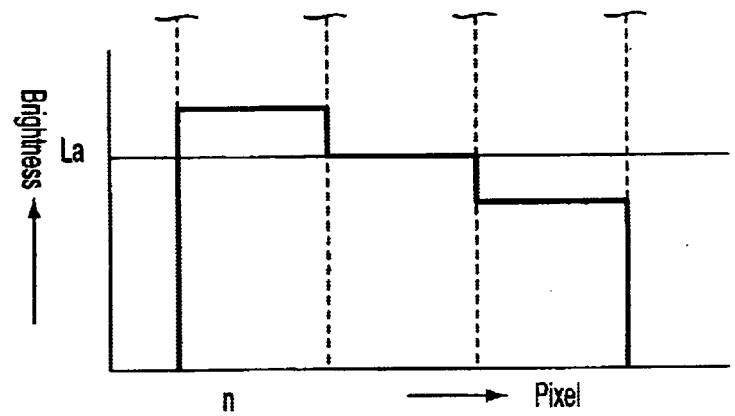
FIG. 3C is a diagrammatic illustration showing the brightness distribution after correction.

Thus, the operation unit 6 obtains the correction factor from the storage unit 5, and implements a corrective operation by way of multiplication with the line Ln' of FIG. 3B. This operation yields the right brightness value (Ln'×La/Ln) for the image. FIG. 3C diagrammatically shows the corrected brightness distribution.

The corrected image is thus displayed in the display unit 300.

With the configuration as described above, the X-ray camera of this invention can substantially improve picture quality of the X-ray image by virtue of canceling errors in brightness caused by inherent dispersion of the sensors and the image detector circuits peculiar to the X-ray camera, through correction of brightness of the image obtained in the photography.

Figure 4:
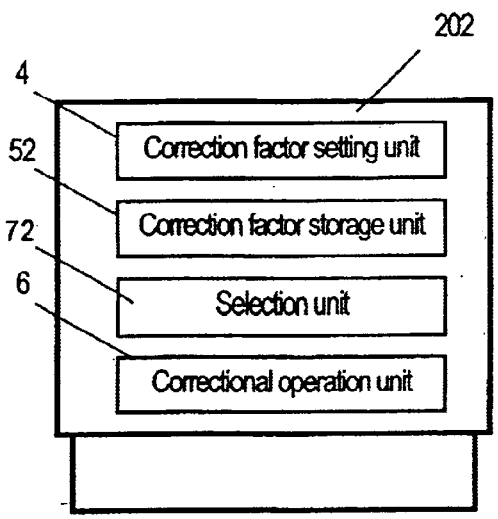
FIG. 4 is an illustration depicting an example of another configuration of the controller shown in FIG. 1.

In this embodiment, as described above, the predetermined brightness reference value (design value) La was used to obtain the correction factor. However, an average value of brightness of the entire image may be used as the reference value La. Alternatively, it is also acceptable to use a representative value of brightness of the entire image (e.g., a maximum value, a mean value, a minimum value, and the like) as the reference value. FIG. 4 shows an example of configuration of the controller in this case.

A setting unit 4 sets correction factors corresponding to three sorts of values, which are:

an average value of brightness;

a representative value of brightness; and a predetermined reference brightness value for each pixel of an image obtained by taking an X-ray photograph of the reference subject. A storage unit 52 stores the three sorts of correction factors set as above. When making correction of brightness of an image obtained by taking an X-ray photograph of a subject body, the operation unit 6 obtains a corresponding correction factor among the three sorts of correction factors through a correction factor selection unit 72 in the storage unit 52.

As described above, brightness characteristic of the X-ray image sensor 2 actually in used can be corrected by virtue of making correction responsive to dispersion of the individual X-ray image sensor. An accuracy of displaying the image can thus be improved. Further, feature of individual operation process determines which one to use between the average value and the representative value. In other words, the average value is used when accuracy is required, and the representative value is used when a high-speed processing is needed.

Furthermore, there results in a better improvement of the accuracy when using the value obtained from the division as La/Ln for the correction factor to be set for each pixel, as compared to the use of a difference like La–Ln, which can be influenced by intensity of external light, illumination, and so on.

As for a reference subject, it may be appropriate to use a soft-tissue equivalent material such as urethane resin and the like to represent muscles and adipose tissue, or a bone-tissue equivalent material such as epoxy resin, aluminum and the like.

Figure 5:
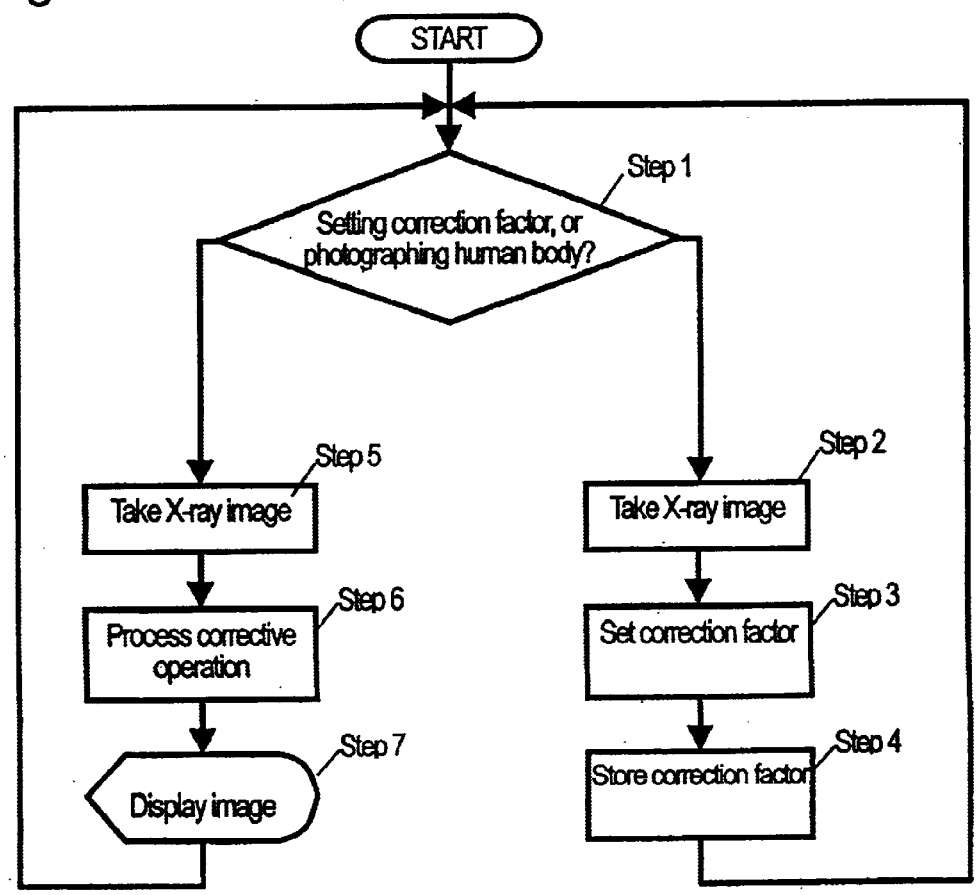
FIG. 5 is a flow chart showing an operational flow of the X-ray camera of the first exemplary embodiment.

Next, FIG. 5 shows an operational flow of the entire X-ray camera of the first exemplary embodiment of this invention.

Upon start of the X-ray camera, a selection is made between setting operation of a correction factor and photographing of a human body (step 1).

If step 1 selects the setting operation of a correction factor at a start of the X-ray camera, the system takes an X-ray photograph of the reference subject 1 (step 2).

The setting unit 4 calculates a correction factor for each pixel based on brightness data of the image obtained in step 2 (step 3).

The correction factor for each pixel obtained in step 3 is stored in the storage unit 5 comprised of a semiconductor memory, a hard disk, and the like (step 4). It returns to the initial state of the system, after the correction factor is stored.

If step 1 selects the subject body to be photographed, it takes an X-ray photograph of the human body (step 5).

The operation unit 6 obtains the correction factor for each pixel from the storage unit 5, and carries out a corrective operation based on the brightness data of the image taken in step 5 (step 6).

The display unit 300 displays the X-ray image after the corrective operation is made in step 6 (step 7).

The above steps 2, 3, and 4 can be initiated at any timing to reset the correction factor, when the equipment is first installed, when a user determines it necessary, and so on. If the correction factor has already been set and stored, the steps 1, 5, 6, and 7 are normally executed.

Second Exemplary Embodiment

A second exemplary embodiment relates to X-ray camera, which sets plural sorts of correction factors to be stored, as described in the first exemplary embodiment. It is so devised as to be capable of selecting which correction factor to use among those correction factors stored in a plurality of storage means, according to thickness of a portion of a human body to be photographed.

A configuration of a controller 202 of the second exemplary embodiment is analogous to the controller 202 shown in the first exemplary embodiment. Although there is a slight difference in function of their respective configurations, the following description will be made in this exemplary embodiment with reference to FIG. 4, since they are analogous in configuration.

The controller 202 of the second exemplary embodiment comprises a setting unit 4, a plurality of storage units 52 capable of storing correction factors, a selection unit 72 for selecting among the storage units 52 a correction factor corresponding to a portion of the subject to be irradiated with X-rays, and an operation unit 6.

In this exemplary embodiment, a photograph is taken by irradiating X rays to a reference subject according to a thickness of photographing portion of a human body to be measured, in the same manner as the first exemplary embodiment.

The setting unit 4 sets correction factors according to the result, in the same manner as the first exemplary embodiment. The storage units 52 then store the correction factors set as above.

When an X-ray photograph is taken for a portion of the subject human body, the operation unit 6 obtains a correction factor for each pixel based on brightness data of the acquired image from one of the storage units 52 that corresponds to the portion of the subject human body, through the selection unit 72, and carries out a corrective operation.

Th display unit 300 displays the X-ray image after the corrective operation is made.

Accordingly, the most appropriate correction factor can be chosen according to thickness of the photographing portion of the human body, when the plurality of correction factors having several sorts of different thicknesses of the reference subject are set and stored.

If photographs are taken for two kinds of equivalent materials, a soft-tissue equivalent material and a bone-tissue equivalent material, for instance, the setting unit 4 sets two sorts of correction factors corresponding to the respective equivalent materials. The storage units 52 store the two sorts of correction factors set as above. When making a correction of brightness of the image acquired by taking an X ray photograph of the subject body, the operation unit 6 obtains a correction factor for each pixel from one of the storage units 52, which corresponds to the portion of the subject human body, through the selection unit 72, and carries out the corrective operation.

Th display unit 300 can then display the X-ray image after the corrective operation is made.

Third Exemplary Embodiment

Figure 6A:
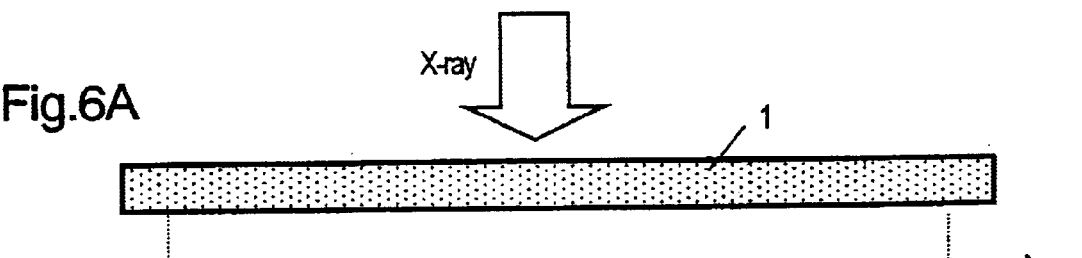
FIG. 6A is an expository illustration depicting operation of X-ray camera having a sensor configuration described in a third exemplary embodiment.

A third exemplary embodiment relates to X-ray camera for taking an X ray photograph with a plurality of X-ray image sensors arranged in an overlapped manner. FIG. 6A shows an example in which a plurality of sensors are arranged so as to overlap with one another at the analogous portions.

Figure 6B:
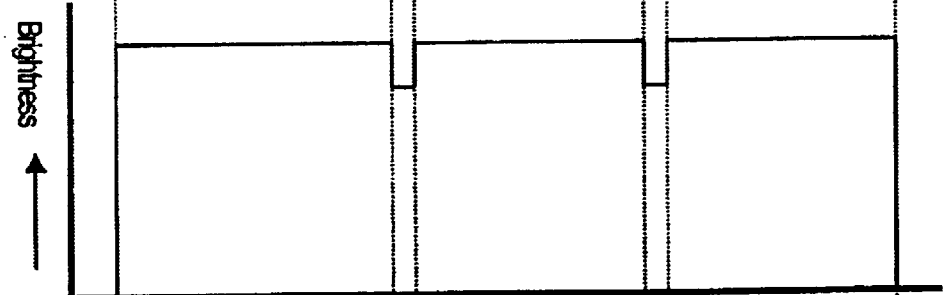
FIG. 6B is a diagrammatic illustration showing an example of brightness distribution of an image, obtained with the X-ray image sensor 2 of the third exemplary embodiment, along a row of pixels in a one-dimensional direction.

As shown in FIG. 6A, three sets of the X-ray image sensor 2 are arranged in a manner that an effective image-capture area (i.e. an area normally narrower than an overall perimeter of the X-ray image sensor) of each of the X-ray image sensors overlaps with one another, in order to detect an image without any dropout portion. It is so designed that an image captured by the sensor located at the front side toward the subject is taken for the image of the overlapped portion. When X rays are irradiated, a portion between an effective image-capture area and a perimeter of the front side sensor gives a shadow on an effective image-capture area of the sensor placed behind the front one, as shown in FIG. 6B. This causes a phenomenon of partially decreasing the brightness only in the area of this shadow. This phenomenon is the largest problem in the X-ray photography with the plurality of X-ray image sensors arranged in the overlapped manner.

Figure 6C:
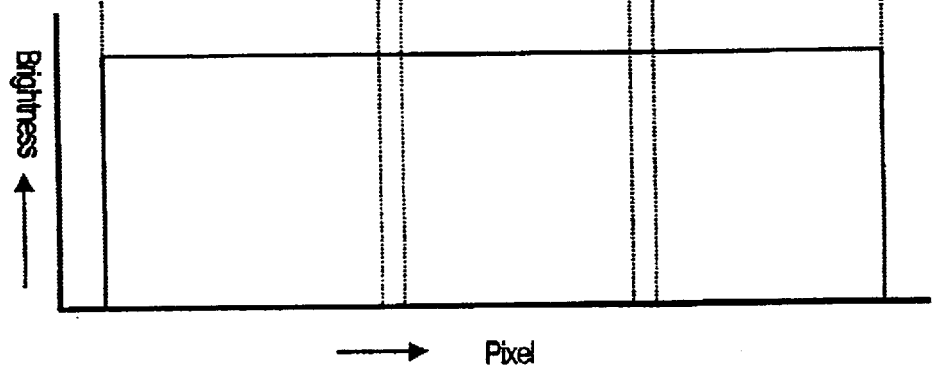
FIG. 6C is a diagrammatic illustration showing the brightness distribution after corrected according to the third exemplary embodiment.

The X-ray camera of the third exemplary embodiment obtains a correction factor for each of arbitrary pixel "n", and carries out a corrective operation for each pixel, in the same manner as described in the first exemplary embodiment. Accordingly, it is proved effective even when the plurality of sensors, arranged in the overlapped manner, are used as the X-ray image sensor, and satisfactory correction of brightness can be achieved, as shown in FIG. 6C.

Fourth Exemplary Embodiment

A fourth exemplary embodiment relates to X-ray camera for taking an X ray photograph with a plurality of X-ray image sensors arranged in an overlapped manner. FIG. 7A shows an example in which a plurality of sensors are arranged in a step-wise manner at the analogous portions.

When X rays are irradiated, a portion between an effective image-capture area and a perimeter of the front side sensor produces a shadow as shown in FIG. 7B on an effective image-capture area of the sensor placed behind the front one, in the like reason as the third exemplary embodiment. This causes a phenomenon of partially decreasing the brightness only in the area of this shadow. This phenomenon is the largest problem in the X-ray photography with the plurality of X-ray image sensors arranged in the overlapped manner.

The X-ray camera of the fourth exemplary embodiment obtains a correction factor for each of arbitrary pixel "n", and carries out a corrective operation for each pixel, in the same manner as described in the first exemplary embodiment. As described, it is proved effective even when the plurality of sensors, arranged in the overlapped manner, are used as the X-ray image sensor, and thereby satisfactory correction of brightness can be achieved, as shown in FIG. 7C.

INDUSTRIAL APPLICABILITY

As has been described, the X-ray camera according to this invention cancels errors in brightness caused by inherent dispersion of the sensors and image detector circuits peculiar to the X-ray camera, by providing a correctional function for brightness of an image obtained in the photography, and thereby it can realize substantial improvement in quality of the X-ray image.

Moreover, it provides for a possibility of correcting image quality precisely according to the subject and portion being photographed, by allowing selection of a method of calculating the correction factor, and a plural kinds of reference subject to be used for setting the correction factor based on a purpose of the photograph.

Accordingly, it is extremely useful for radiographic diagnosis in the medical field.

In addition, it is also adaptable for the correction of brightness in the overlapped area of sensors, in the case of equipment that uses a combination of plural sensors for the purpose of obtaining a wide photographable area, and therefore it is extremely useful again for radiographic diagnosis in the medical field.

What is claimed is:

1. An X-ray camera comprising:
   an X-ray irradiation unit;
   an X-ray image sensor including an X-ray-to-photo conversion device for converting an X-ray radiated from said X-ray irradiation unit to a photo signal for corresponding to an intensity of the X-ray and a photoelectric conversion device for converting the photo signal to an electric signal to output brightness data of an image in a unit of a pixel;
   a correction factor setting unit for setting a correction factor based on electronic image data of a reference subject provided from said X-ray image sensor which takes an X-ray photograph of the reference subject;
   a correction factor storage unit for storing the correction factor set in said correction factor setting unit; and
   a controller for correcting the brightness data of the image output from said X-ray image sensor based on the correction factor to output corrected brightness data.

2. The X-ray camera as set forth in claim 1, wherein said correction factor for improvement of picture quality acquired from the brightness data of the image obtained by taking the X-ray photograph of said reference subject is set therein for each pixel individually.

3. The X-ray camera as set forth in claim 2, wherein a value acquired by dividing a predetermined brightness reference value with a brightness value of each pixel in the image obtained by taking the X-ray photograph of said reference subject is used as a correction factor for said pixel.

4. The X-ray camera as set forth in claim 3, wherein said controller corrects the brightness of each pixel by multiplying a brightness value of said pixel in the image obtained by taking the X-ray photograph of a subject body by said correction factor of the corresponding pixel.

5. The X-ray camera as set forth in claim 2, wherein a value acquired by dividing an average value of brightness of the image obtained by taking the X-ray photograph of said reference subject with the brightness value of each pixel is used as a correction factor for said pixel.

6. The X-ray camera as set forth in claim 5, wherein said controller corrects the brightness of each pixel by multiplying a brightness value of said pixel in the image obtained by taking the X-ray photograph of said reference subject by said correction factor of the corresponding pixel.

7. The X-ray camera as set forth in claim 2, wherein a value acquired by dividing a representative value of brightness of the image obtained by taking the X-ray photograph of said reference subject with the brightness value of each pixel is used as a correction factor for said pixel.

8. The X-ray camera as set forth in claim 7, wherein said controller corrects brightness of each pixel by multiplying a brightness value of said pixel in the image obtained by taking the X-ray photograph of said reference subject by said correction factor of the corresponding pixel.

9. The X-ray camera as set forth in claim 2, wherein urethane resin for typifying a soft-tissue equivalent material representing muscles and adipose tissue, composed of urethane resin and the like, is used as the reference subject.

10. The X-ray camera as set forth in claim 2, wherein any of epoxy resin and aluminum typifying a bone-tissue equivalent material is used as the reference subject.

11. The X-ray camera as set forth in claim 2 further comprising a correction factor setting means for setting a correction factor, other than ordinary X-ray photography, in order to acquire said correction factor, wherein said X-ray camera can be operated for resetting a correction factor for improvement of picture quality at an arbitrary timing when said equipment is first installed, when a user determines it necessary.

12. The X-ray as set forth in claim 1
wherein said correction factor storage unit stores three types of correction factors obtained by dividing each of three values by a brightness value of each pixel, said three values being an average value and a representative value of brightness of an image obtained by taking the X-ray photograph of said reference subject, and a predetermined reference brightness value, and said controller selects one correction factor among said three types of correction factors when making correction of brightness of the image obtained by taking the X-ray photograph of said reference subject.

13. The X-ray camera as set forth in claim 1
wherein said correction factor storage means stores two types of correction factors corresponding to a soft-tissue equivalent material and a bone-tissue equivalent material by taking photographs of said two equivalent materials, and said controller selects one correction factor between said two types of correction factors when making correction of brightness of the image obtained by taking the X-ray photograph of said reference subject.

14. The X-ray camera as set forth in claim 1, wherein a plurality of X-ray image sensors are arranged in a manner that a portion of an image-capture area of each said sensor overlaps with one another, in order to take an X-ray image of an expanded size without an error of brightness in the overlapped portion.

15. The X-ray camera as set forth in claim 1, wherein a thickness of the reference subject is uniform.

16. The X-ray camera as set forth in claim 1, wherein a material of reference subject is homogeneous.

* * * * *